United States Patent
Chen et al.

(10) Patent No.: US 12,360,096 B2
(45) Date of Patent: Jul. 15, 2025

(54) **SCREENING METHOD FOR DROUGHT-RESISTANT GERMPLASM OF *OPHIOPOGON JAPONICUS***

(71) Applicant: Sichuan Academy of Chinese Medicine Sciences, Chengdu (CN)

(72) Inventors: Tiezhu Chen, Chengdu (CN); Juan Lin, Chengdu (CN); Xia Zhou, Chengdu (CN); Jianhui Liu, Chengdu (CN); Tingting Cheng, Chengdu (CN)

(73) Assignee: Sichuan Academy of Chinese Medicine Sciences, Chengdu (CN)

( * ) Notice: Subject to any disclaimer, the term of this patent is extended or adjusted under 35 U.S.C. 154(b) by 0 days.

(21) Appl. No.: 18/638,701

(22) Filed: Apr. 18, 2024

(65) Prior Publication Data
US 2025/0020622 A1    Jan. 16, 2025

(30) Foreign Application Priority Data
Jul. 13, 2023   (CN) .......................... 202310857324.6

(51) Int. Cl.
| | |
|---|---|
| *G01N 33/00* | (2006.01) |
| *C12Q 1/28* | (2006.01) |
| *C12Q 1/30* | (2006.01) |
| *G01N 33/68* | (2006.01) |
| *G16B 25/10* | (2019.01) |
| *G16Z 99/00* | (2019.01) |

(52) U.S. Cl.
CPC .......... *G01N 33/0098* (2013.01); *C12Q 1/28* (2013.01); *C12Q 1/30* (2013.01); *G01N 33/68* (2013.01); *G16B 25/10* (2019.02); *G01N 2333/908* (2013.01); *G16Z 99/00* (2019.02)

(58) Field of Classification Search
CPC .............. G01N 33/0098; G01N 33/68; G01N 2333/908; C12Q 1/28; C12Q 1/30; G16B 25/10; G16Z 99/00
See application file for complete search history.

(56) References Cited

FOREIGN PATENT DOCUMENTS

| | | | |
|---|---|---|---|
| CN | 1047279 C | * | 12/1999 |
| CN | 110367067 A | | 10/2019 |

OTHER PUBLICATIONS

Fu Q, Li B, Yang L, Wu Z, Zhang X. Ecosystem Services Evaluation and Its Spatial Characteristics in Central Asia's Arid Regions: A Case Study in Altay Prefecture, China. Sustainability. 2015; 7(7):8335-8353. https://doi.org/10.3390/su7078335 (Year: 2015).*

Du, Feng et al. "Responses of reactive oxygen scavenging enzymes, proline and malondialdehyde to water deficits among six secondary successional seral species in Loess Plateau." PloS one vol. 9,6 e98872. Jun. 10, 2014, doi:10.1371/journal.pone.0098872 (Year: 2014).*

Guozhong, Meng, and Jiang Li. "Comprehensive Evaluation on Drought Resistance of Some Ground Covers." 2009 Second International Conference on Information and Computing Science. vol. 4. IEEE, 2009. (Year: 2009).*

Zhang, Weihua, Chaofu Wei, and Jia Zhou. "Optimal allocation of rainfall in the Sichuan Basin, Southwest China." Water resources management 24 (2010): 4529-4549. (Year: 2010).*

Fan Hailan et al., Response of Liriope Muscari (Decne.) Bailey of Fujian genuine Medicine to Water Stress and Nitrogen Deposition, The Full Text Database of Chinese Doctoral Dissertations (Agricultural Science and Technology. Edition), Apr. 2015, issue 4, full text.

* cited by examiner

Primary Examiner — Larry D Riggs, II
Assistant Examiner — Kettip Kriangchaivech

(57) ABSTRACT

A screening method for a drought-resistant germplasm of *Ophiopogon japonicus* related to the field of *Ophiopogon japonicus* planting is provided. The method uses *Ophiopogon japonicus* of the main production areas, which requires a large amount of water and rainfall during the growth period, the drought-resistant germplasm that is suitable for growing well is conducted with drought stress under the drought condition. The growth indicators and the physiological indicators of different *Ophiopogon japonicus* germplasm under drought stress conditions are comprehensively evaluated and ranked to evaluate the drought-resistant ability of the different germplasm. The screening method is scientific and effective, and can comprehensively evaluate the drought resistance ability of *Ophiopogon japonicus* under the drought stress conditions, laying a technical foundation for the screening and promotion of in the *Ophiopogon japonicus* with drought resistance ability.

4 Claims, No Drawings

SCREENING METHOD FOR DROUGHT-RESISTANT GERMPLASM OF *OPHIOPOGON JAPONICUS*

TECHNICAL FIELD

The disclosure relates to the field of *Ophiopogon japonicus* planting, and particularly to a screening method for a drought-resistant germplasm of *Ophiopogon japonicus*.

BACKGROUND

In long-term field cultivation, it was observed that drought and water scarcity are extremely detrimental to the growth and development of the traditional Chinese medicine of *Ophiopogon japonicus* (L. f.) Ker Gawl. Drought stress is one of the most harmful natural disasters of all, and its impact on medicinal plants is greater than the sum of other abiotic stresses. The drought stress is an important ecological and environmental factor that limits plant growth, development, and economic value. The annual losses caused by drought in medicinal plants in China are incalculable. Under natural conditions, the *Ophiopogon japonicus* prefers moist soil, especially during the period of nutritive root development (late April to mid-June), sprouting is vigorous and the underground part of the *Ophiopogon japonicus* is sprouting new roots, requiring a large amount of water. When drought occurs during the period, newly planted seedlings cannot quickly sprout new roots, resulting in multitudinous dead plants due to water scarcity. The rooted seedlings can also have withered and yellowed leaves due to the drought, affecting their growth and development.

As the main production area of traditional Chinese medicine of the *Ophiopogon japonicus* in China, Santai County, Mianyang City, Sichuan Province, accounts for over 70% of the country's medicinal materials of the *Ophiopogon japonicus*. In 2014, 2016, 2018, 2020, and 2022, the main production areas of the *Ophiopogon japonicus* in Santai County, Mianyang City had less spring rainfall, and drought and water shortage were serious. To alleviate the impact of drought and water shortage on the growth and development of the *Ophiopogon japonicus*, the production areas adopt multiple irrigation methods or add a large amount of water during fertilization to ensure that the soil can maintain a relatively moist state frequently, in order to compensate for the insufficient rainfall and uneven distribution of precipitation. However, it incurs a lot of labor costs, and the drought resistance effect is not significant. In the year of drought in spring, the loss of the *Ophiopogon japonicus* industry exceeded billions. Therefore, it is crucial to screen drought-resistant germplasm of the *Ophiopogon japonicus*.

At present, there is no report on the screening method for drought-resistant germplasm of *Ophiopogon japonicus*. The reported studies on drought resistance of *Ophiopogon japonicus* focus on the physiological response of *Liriope muscari* (Decne.) L. H. Bailey under drought stress, rather than the traditional Chinese medicine of *Ophiopogon japonicus* (L. f.) Ker Gawl. The current reported drought-resistant methods for *Ophiopogon japonicus* include artificial simulation of water stress, polyethylene glycol 6000 (PEG6000) simulation of drought stress, and comparison of drought resistance between *Ophiopogon japonicus* and other garden ornamental plants through membership function evaluation. However, in the aforementioned studies, *Ophiopogon japonicus* was used as a garden ornamental plant rather than the original plant of traditional Chinese medicine of *Ophiopogon japonicus*, and the water application amount and source under drought conditions were not clearly explained. Therefore, there is an urgent need for a scientific and effective screening method for drought-resistant germplasm of *Ophiopogon japonicus*.

SUMMARY

A screening method for drought-resistant germplasm of *Ophiopogon japonicus* is provided to solve the problems existing in the related art.

To achieve the above objectives, the technical solutions are as follows.

A screening method for a drought-resistant germplasm of *Ophiopogon japonicus* is provided and includes the following steps:

(1) collecting surviving *Ophiopogon japonicus* from a cultivated field and a wild condition under drought, introducing the collected surviving *Ophiopogon japonicus* to a conservation nursery of *Ophiopogon japonicus* germplasms, and selecting populations of the *Ophiopogon japonicus* germplasms with consistent apparent epigenetic trait in the conservation nursery of *Ophiopogon japonicus* germplasms for further evaluation after the introducing;

(2) using an online geographic information system (GIS) software (ArcGIS 10.2®) to extract rainfall of a main production area of the *Ophiopogon japonicus* during a period of water demands for growth of the *Ophiopogon japonicus*, calculating monthly average rainfall, and converting the monthly average rainfall into a water supply;

(3) setting 100±5% (i.e., 95%-105%), 50±5% (i.e., 45%-55%), and 35±5% (i.e., 30%-40%) of the water supply converted in the step (2) as a normal water supply, a moderate drought, and a severe drought of three water gradients according to the period of the water demands for the growth of the *Ophiopogon japonicus* under a natural condition, respectively; conducting drought stress simulation experiments on the populations of the *Ophiopogon japonicus* germplasms obtained in the step (1) under different drought conditions;

(4) after setting the three water gradients, determining growth indicators and physiological indicators of the populations of the *Ophiopogon japonicus* germplasms under different drought stress conditions; wherein the growth indicators include chlorophyll, a number of new roots, length of the new roots, a number of leaves, width of the leaves, and growth of leaf length, the physiological indicators include malondialdehyde (MDA), total superoxide dismutase (SOD), peroxidase (POD), catalase (CAT), and proline (Pro); and (5) applying fuzzy mathematical evaluation method to comprehensively rank the growth indicators and the physiological indicators of the populations of the *Ophiopogon japonicus* germplasm, thereby evaluating a drought-resistant ability of the *Ophiopogon japonicus* and screening out the drought-resistant germplasm of the *Ophiopogon japonicus*.

In an embodiment, the period of high water demand for the growth of *Ophiopogon japonicus* is from April to June each year.

In an embodiment, a standard of the drought in the step (1) is: a landmass of the cultivated field with high terrain and no water storage or a slope under a wild forest, and a soil moisture content of less than 20%; criteria of judging the surviving *Ophiopogon japonicus* are: plants of the *Ophiopogon japonicus* grows vigorously, and the leaves of the *Ophiopogon japonicus* appear green and not withered yellow; the consistent apparent epigenetic trait indicates that the leaves of the plants from a same production area have a same color, and statistically significant differences in a plant height, the number of leaves, the widths of leaves, the leaf length, and a number of tillers are non-statistical difference.

In an embodiment, the main production area in the step (2) of the *Ophiopogon japonicus* includes Luxi Town, Laoma Town, Licheng Town, Lingxing Town, Liuying Town, Xinde Town, Yongming Town, and Jianshe Town in Santai County, Mianyang City, Sichuan Province, China; the monthly average rainfall is converted into the water supply daily per pot, and a converting formula is as follows:

the water supply=the monthly average rainfall(millimeter)×0.667(square meters)÷30 (days)÷an area of an experimental container(square meters).

In an embodiment, in the step (4), the growth indicators include chlorophyll, a number of new roots, lengths of the new roots, a number of leaves, widths of the leaves, and growth of leaf length.

In an embodiment, in the step (4), the physiological indicators include malondialdehyde (MDA), total superoxide dismutase (SOD), peroxidase (POD), catalase (CAT), and proline (Pro).

In an embodiment, a scoring method of consulting industry experts to screen and assign the growth indicators and the physiological indicators is adopted, and a specific allocation of weights is as follows:

the chlorophyll (0.20), the number of new roots (0.05), the lengths of the new roots (0.05), the number of leaves (0.03), the widths of the leaves (0.03), and the growth of leaf length (0.04), MDA (0.12), SOD (0.12), POD (0.12), CAT (0.12), and Pro (0.12);

a comprehensive evaluation of the fuzzy mathematical evaluation method is applied to evaluate the drought-resistant ability of the populations of the *Ophiopogon japonicus* under the moderate drought and the severe drought of the drought stress conditions, and the drought-resistant ability of the populations of the *Ophiopogon japonicus* germplasms is ranked.

The technical effects of the disclosure are as follows.

In the disclosure, for the *Ophiopogon japonicus* of the main production area requiring a large amount of water and rainfall during the growth period, the drought-resistant germplasm that is suitable for growing well is conducted with drought stress under the drought condition. The growth indicators and the physiological indicators of different *Ophiopogon japonicus* germplasm under drought stress conditions are comprehensively ranked to evaluate the drought-resistant ability of the different germplasm. The screening method is scientific and effective, and can comprehensively evaluate the drought-resistant ability of *Ophiopogon japonicus* under the drought stress conditions, laying a technical foundation for the screening and promotion of the *Ophiopogon japonicus* germplasm.

DETAILED DESCRIPTION OF EMBODIMENTS

Multiple exemplary embodiments of the disclosure are described in detail. In the embodiments, conventional methods are used unless otherwise specified, and reagents used are either commercially available or prepared using conventional methods. This detailed description should not be considered as a limitation of the disclosure but should be understood as a more detailed description of certain aspects, features, and embodiments of the disclosure.

It should be understood that the terms described in the disclosure are only for describing specific embodiments and are not intended to limit the disclosure. Furthermore, for the numerical range in the disclosure, it should be understood that each intermediate value between the upper and lower limits of the range is also specifically disclosed. Each of the smaller ranges within any stated value or intermediate value within the stated range, and any other stated value or intermediate value within the stated range, is also included within the disclosure. The upper and lower limits of these smaller ranges may be independently included or excluded from the range.

Unless otherwise specified, all technical and scientific terms used in the disclosure have the same meanings as those commonly understood by those skilled in the art described herein. Although the disclosure only describes specific methods and materials, any methods and materials similar or equivalent to those described herein may also be used in the implementation or testing of the disclosure. All literatures mentioned in the specification is incorporated by reference to publicly disclose and describe methods and/or materials related to the literature. In case of conflict with any incorporated literature, the content of the specification shall prevail.

It is evident to those skilled in the art that various improvements and variations can be made to the specific embodiments of the disclosure without departing from the scope or spirit of the disclosure. The other embodiments obtained from the specification of the disclosure are obvious to those skilled in the art. The specification of the disclosure and embodiments are only illustrative.

The terms "include", "comprise", "have" and "contain" used in the disclosure are all open-ended terms, meaning to include but not limited to.

The technical solutions described in the disclosure, unless otherwise specified, are conventional solutions in the art. The reagents or raw materials used, unless otherwise specified, are purchased from commercial channels or have been disclosed.

Embodiment 1

Collect *Ophiopogon japonicus* in the period of maximum water demand for the growth from April to June Plants of the *Ophiopogon japonicus* cultivated in a landmass of the cultivated field with high terrain and no water storage or a slope under a wild forest are collected, with a soil moisture content below 20%. The plants of *Ophiopogon japonicus* with vigorous growth and green, non-yellowing leaves are introduced to a conservation nursery of *Ophiopogon japonicus* germplasm. After introducing suitable germplasm of *Ophiopogon japonicus*, a population of *Ophiopogon japonicus* germplasms with consistent plant color, plant height, number of leaves, leaf width, leaf length, and number of tillers is selected that can be further evaluated.

11 different germplasm resources of *Ophiopogon japonicus* (L. f.) Ker Gawl. are collected from different production areas such as Sichuan, Hubei, and Guizhou, among which 6 germplasm resources are wild germplasm resources. The specific origin information of each number is shown in Table 1.

TABLE 1

11 germplasm resources of *Ophiopogon japonicus* with drought-resistant ability from different areas

| Number | Collecting areas | Type of *Ophiopogon japonicus* | Longitude | Latitude |
|---|---|---|---|---|
| A | Hejiagou, Jianshe Town, Santai County, Sichuan Province, China | Erect type | 104.9481 | 31.3009 |
| B | Wulong Village, Laoma Town, Santai County, Sichuan Province, China | Erect type | 105.0098 | 31.2438 |
| C | Baiduo Township, Shibing County, Qiandongnan Prefecture, Guizhou Province, China | Erect type | 108.1135 | 27.1029 |
| D | Pengjiaji, Luxi Town, Santai County, Sichuan Province, China | creeping type | 104.8905 | 31.3219 |
| E | Wulong Village, Laoma Town, Santai County, Sichuan Province, China | Erect type | 105.0047 | 31.2456 |
| F | Zaohe Village, Luxi Town, Santai County, Sichuan Province, China | Erect type | 104.9001 | 31.3181 |
| G | Pengjiaji, Luxi Town, Santai County, Sichuan Province, China | Erect type | 104.8905 | 31.3219 |
| H | Group 8, Jufeng Village, Qingquan Town, Qingbaijiang District, Chengdu City, Sichuan Province, China | Erect type | 104.3862 | 30.7433 |
|  |  |  |  | 30.8491 |
| I | Puzhao Temple, Mount Qingcheng, Daguan Town, Dujiangyan City, Chengdu City, Sichuan Province, China |  | 103.5580 |  |
| J | Ziling Town, Dongbao District, Jingmen City, Hubei Province, | Erect type | 112.2232 | 31.1164 |
| K | Longtanhe Town, Cili County, Zhangjiajie City, Hubei Province, China | Erect type | 111.0805 | 29.2393 |

1. Data Source of Distribution Points of Main Production Areas of *Ophiopogon japonicus*

Based on preliminary investigation and research, the information (longitude and latitude) of planting areas of *Ophiopogon japonicus* in the main production areas of Luxi Town, Laoma Town, Licheng Town, Lingxing Town, Liuying Town, Xinde Town, Yongming Town, and Jianshe Town in Santai County, Mianyang City, Sichuan Province, China is compiled.

2. Data Format Conversion

The "Add Data" function in the "File" menu of the online GIS software (ArcGIS 10.2®) is used to convert data saved in the format of "longitude+latitude" excel (.xls) format to shapefile (.shp) format.

3. Ecological Factor Extraction

The (.shp) format data is loaded into the online GIS software (ArcGIS 10.2®), and the function of "Multi value Extraction to Point" of "Extraction analysis" of "Spatial Analysis Tools" in the Arc Toolbox is used to input the grid format of three climate ecological factors, including April rainfall (pre_4), May rainfall (pre_5), and June rainfall (pre_6), from the global climate database of WorldClim 2.0 with a resolution of 30 seconds, and the rainfall values from April to June in the main production area of *Ophiopogon japonicus* in Santai County, Mianyang City, Sichuan Province, China are extracted. The extraction results are shown in Table 2, and the average monthly rainfall from April to June is calculated to be 85 millimeters (mm).

TABLE 2

Rainfall in the main production area of *Ophiopogon japonicus* from April to June (mm)

| Longitude | Latitude | pre_4 | pre_5 | pre_6 |
|---|---|---|---|---|
| 104.917215 | 31.301442 | 50 | 87 | 116 |
| 104.956022 | 31.277270 | 50 | 87 | 117 |
| 105.102744 | 31.211301 | 52 | 91 | 123 |
| 105.000357 | 31.269928 | 51 | 89 | 118 |
| 104.985332 | 31.280097 | 51 | 88 | 118 |
| 105.042581 | 31.118872 | 52 | 91 | 124 |
| 105.042581 | 31.118872 | 52 | 91 | 124 |
| 104.999272 | 31.237999 | 51 | 89 | 120 |
| 105.011002 | 31.166981 | 51 | 89 | 120 |
| 104.985606 | 31.215878 | 51 | 89 | 118 |
| 104.881641 | 31.263915 | 49 | 87 | 116 |
| 104.895738 | 31.296952 | 49 | 86 | 115 |
| 104.883966 | 31.311342 | 49 | 86 | 114 |
| 105.064465 | 31.153594 | 52 | 90 | 121 |
| 105.046797 | 31.146638 | 52 | 90 | 120 |
| 104.897430 | 31.379139 | 49 | 86 | 114 |
| 104.887415 | 31.353280 | 49 | 86 | 113 |
| 105.029129 | 31.187893 | 52 | 90 | 121 |
| 104.948152 | 31.300909 | 50 | 88 | 117 |
| 104.900113 | 31.318114 | 49 | 86 | 115 |
| 104.899034 | 31.319568 | 49 | 86 | 114 |
| 104.873290 | 31.357831 | 49 | 86 | 112 |
| 104.869018 | 31.356220 | 49 | 86 | 112 |
| 104.897137 | 31.340201 | 49 | 86 | 114 |
| 104.890590 | 31.321903 | 49 | 86 | 113 |
| 104.968324 | 31.268034 | 50 | 88 | 117 |
| 105.009895 | 31.243841 | 51 | 89 | 119 |
| 104.982122 | 31.223717 | 51 | 89 | 118 |
| 105.020269 | 31.151054 | 51 | 90 | 119 |

From Table 2, it can be seen that the average rainfall in the main production area of *Ophiopogon japonicus* from April to June is 85 mm. According to the monthly average rainfall of 85 mm, the average rainfall is converted into a water supply daily per pot in the embodiment using formula (1), and the converting formula is as follows:

the water supply = the monthly average rainfall (millimeter) × 0.667 (square meters) ÷ 30

(days) ÷ an area of an experimental container (square meters).

The conversion results are as follows:

normal water supply: water every day of the week with a water supply of 213.1 milliliters (mL) per pot each time;

moderate drought: water every day of the week with a water supply of 106.5 mL per pot each time; and severe drought: water every day of the week with a water supply of 74.6 mL per pot each time.

Embodiment 2

Comprehensive evaluation and screening of drought-resistant germplasm of *Ophiopogon japonicus*

The experimental reagents used in the embodiment mainly include: a specific reagent kit for measuring malondialdehyde (MDA), total superoxide dismutase (SOD), peroxidase (POD), catalase (CAT), and proline (Pro) in leaves of *Ophiopogon japonicus* (from Nanjing Jiancheng Biotechnology Research Institute); acetic acid (analytical grade, acetic acid concentration>99.5%).

MDA assay kit (100 tubes/96 samples, i.e., 100 T/96 s, A003-1-2) includes four reagents. Reagent 1: liquid of 20 mL×1 bottle, colorless and transparent, can be solidified at a low temperature, stored at room temperature. Reagent 2: liquid of 12 mL×1 bottle, colorless and transparent, refrigerated and stored at 4° C. Reagent 3: powder×1, light yellow or white, refrigerated and stored at 4° C. in dark. Standard product: 10 nanomoles per milliliter (nmol/mL) of tetraethoxypropane 5 mL×1 bottle, colorless and transparent, refrigerated and stored at 4° C.

SOD assay kit (A001-3-2: 95T) includes four reagents. Reagent 1: a buffer solution, liquid of 15 mL×2 bottle, colorless and transparent, stored at 4° C. Reagent 2: substrate stock solution, liquid of 0.15 mL×1, brown, stored at 4° C. Reagent 3: enzyme stock solution, 0.30 mL×1, colorless and transparent, stored at 4° C. Reagent 4: enzyme diluent, light brown, liquid of 4 mL×1 bottle, refrigerated at −20° C.

Pro assay kit (A107-1-1, 50 T/48 s) includes four reagents. Reagent 1:60 mL×2 bottle, stored at 4° C. in dark. Reagent 2: a buffer solution, 60 mL×1 bottle, stored at 4° C. in dark. Reagent 3:60 mL×1 bottle, stored at 4° C. in dark. Standard product: 100 micrograms per milliliter (μg/mL) of a standard stock solution, 1 mL×1, stored at 4° C.

CAT assay kit (A007-1-1, ammonium molybdenum acid method) includes four reagents. Reagent 1: liquid of 100 mL×1 bottle, colorless and transparent, stored at 4° C. Reagent 2: substrate liquid of 10 mL×1 bottle, colorless and transparent, stored at 4° C. Reagent 3: color developing powder×1 bottle, white, stored at 4° C., the color developing powder is dissolved in 100 mL of double distilled water and stored at 4° C. for 1 month. (when there is insoluble powder precipitation at the bottom of the dissolved double distilled water, the supernatant of the dissolved double distilled water can be directly used without affecting the testing results) Reagent 4: liquid of 10 mL×1 bottle, colorless and transparent, solidified at low temperature, and stored at 4° C. When the weather is cold, the reagent 4 will solidify, before use, the reagent 4 can be heated at 37° C. until it is transparent.

POD assay kit (A084-3-1, testing plants) includes four reagents. Reagent 1:60 mL of liquid×4 bottles, colorless and transparent, stored at 4° C. Reagent 2: powder×3 bottles, white, stored at 4° C. Reagent 3: liquid of 5 mL×1 bottle, colorless and transparent, stored at 4° C. Reagent 4: liquid of 50 mL×2 bottle, colorless and transparent, stored at 4° C.

1. Test of Drought-Resistant Ability of Different Germplasms of *Ophiopogon japonicus*

The test is conducted using the potted plant simulation water control method, which is set up on the high transparency balcony of Sichuan Academy of Chinese Medicine Sciences. The flower pot is a rectangular flower pot for Zhiyu brand horticultural planting, with a specification of 47 centimeters (cm) in length, 19 cm in width, and 16 cm in height, 10 germplasms of *Ophiopogon japonicus* per pot, with replication of 3 times. The plant height of *Ophiopogon japonicus* is 20 cm. Matrix formula: organic matter content is 1.80 grams per kilogram (g/kg), total nitrogen (N) is 2.5 g/kg, total phosphorus (P) is 1.5 g/kg, pondus hydrogenii (pH) value is 6.8, and the maximum water holding capacity of the matrix is 25.8%.

The drought-resistant test is set up three water gradients, namely normal water supply (CD), moderate drought (MD), and severe drought (SD), with the amount of the water supply controlled at 100±5%, 50±5%, and 35±5% of the average rainfall (85 mm), respectively. Before and after the Tomb Sweeping Day in China, the 11 surviving germplasm populations of *Ophiopogon japonicus* (with similar growth conditions and development stages) from the conservation nursery of *Ophiopogon japonicus* germplasms are selected and transplanted into experimental pots. After transplanting, and the plants of *Ophiopogon japonicus* are fully irrigated.

2. Determination of Growth Indicators

When the plants of *Ophiopogon japonicus* are in the stage of nutritive root development in late April, water control should be carried out as follows.

normal water supply: water every day of the week with a water supply of 213.1 mL per pot each time;

moderate drought: water every day of the week with a water supply of 106.5 mL per pot each time;

severe drought: water every day of the week with a water supply of 74.6 mL per pot each time.

After the formation of drought gradients (that is, a soil moisture content of the normal water supply is 20.4%-25.4%, a soil moisture content of the moderate drought is 12.2%-14.9%, and a soil moisture content of the severe drought is 5.0%-9.8%), growth indicators such as survival rate, chlorophyll content, number of new roots, length of new roots, number of leaves, leaf widths, and growth of leaf length are measured. The chlorophyll content is measured using chlorophyll meter SPAD-502 plus produced by Konica Minolta, and the survival rate is measured by counting the number of laboratory technicians and the widths of leaves are measured using a vernier caliper, the remaining indicators are measured using a ruler.

2.1 Survival Rate Measurement

The survival rate measurement results are shown in Table 3.

TABLE 3

Effect of drought stress on the survival rate of different germplasms of *Ophiopogon japonicus*

| Serial number of germplasm resource | Normal water supply (CD) | Moderate drought (MD) | Severe drought (SD) |
|---|---|---|---|
| A | 10+++ | 10++ | 10++ |
| B | 10+++ | 10+ | 10+ |
| C | 10+++ | 10+++ | 10+++ |
| D | 10+++ | 10+++ | 10+++ |
| E | 10+++ | 10++ | 10++ |
| F | 10+++ | 10++ | 10++ |
| G | 10+++ | 10+ | 10+ |
| H | 10+++ | 10+ | 10+ |
| I | 10+++ | 10+ | 10+ |
| J | 10+++ | 10+++ | 10+++ |
| K | 10+++ | 10+++ | 10+++ |

Note:
+++represents vigorous growth, and the overall leaves are "green";
++represents good growth, with very few germplasm leaves turning yellow, and the overall color of the leaves is "green + partially yellow green";
+represents poor growth, with most germplasm leaves turning yellow and the overall color of the leaves being "yellow green".

From the Table 3, it can be seen that all germplasms survived under different drought conditions, but the growth status of plants is not entirely the same. The germplasm C, germplasm D, germplasm J, and germplasm K exhibit a relatively vigorous plant state under various drought stress conditions, with overall green leaves, among which the Germplasm D is a creeping type. The Germplasm A, germplasm E, and germplasm F show little change in plant performance with the intensification of drought, and their leaves turn into a "green+partially yellow green" state, which indicates good drought resistance. As the degree of drought increases, the leaf color of the germplasm B, germplasm G, germplasm H, and germplasm I turns yellow green, which indicates weak drought resistance.

2.2 Chlorophyll Content Determination

In order to further demonstrate the issue of leaf discoloration, the chlorophyll contents in all test leaves of *Ophiopogon japonicus* are measured, and the results are shown in Table 4.

TABLE 4

Effect of drought stress on chlorophyll in leaves of different germplasms of *Ophiopogon japonicus* (SPAD)

| Serial number of germplasm resource | Normal water supply (CD) | Moderate drought (MD) | Severe drought (SD) | MD-CD | SD-CD |
|---|---|---|---|---|---|
| A | 52.9a | 40.1b | 39.4b | −12.8 | −13.5 |
| B | 53.2a | 32.5b | 20.2c | −20.7 | −33 |
| C | 51.0a | 43.5b | 44.3b | −5.5 | −6.7 |
| D | 53.6a | 49.9a | 48.5a | −3.7 | −5.1 |
| E | 55.4a | 45.5b | 43.3b | −9.9 | −12.1 |
| F | 48.5a | 34.2b | 31.5b | −14.3 | −17 |
| G | 54.5a | 34.9b | 23.5c | −19.6 | −31 |
| H | 49.3a | 37.3b | 25.6c | −12 | −23.7 |
| I | 43.9a | 34.9b | 25.8c | −9 | −18.1 |
| J | 56.7a | 53.9a | 51.2a | −2.8 | −5.5 |
| K | 52.4a | 49.0a | 48.1a | −3.4 | −4.3 |

Note:
The same letter after the same row of data indicates no significant difference, and different letters indicate significant differences (P < 0.05), which is applied to the following tables.

As shown in Table 4, drought stress can lead to inhibition of chlorophyll synthesis or chlorophyll degradation. The reason may be that under drought stress, the water content inside the leaf cells decreases, and the rate of chlorophyll synthesis slows down, which affects the formation of ribosomes, hinders protein synthesis, slows metabolism, inhibits chlorophyll biosynthesis, and chlorophyll is broken down. The Germplasm C, germplasm D, germplasm J, and germplasm K show little decrease in chlorophyll content compared to the normal water supply under drought stress conditions, consistent with the overall green color of the leaves, which indicates strong drought resistance. Under drought stress conditions, the germplasm B, germplasm G, germplasm H, and germplasm I show significant differences from the normal water supply, which indicates poor drought resistance.

2.3 Determination of Number of New Roots

The effect of drought stress on the number of new roots of *Ophiopogon japonicus* is shown in Table 5.

TABLE 5

Effect of drought stress on the number of new roots in different germplasm of *Ophiopogon japonicus*

| Serial number of germplasm resource | Normal water supply (CD) | Moderate drought (MD) | Severe drought (SD) |
|---|---|---|---|
| A | 2.1a | 2.2a | 2.4a |
| B | 2.2a | 2.3a | 2.5a |
| C | 2.0b | 2.2b | 2.9a |
| D | 2.0b | 2.3b | 3.0a |
| E | 2.2a | 2.4a | 2.5a |
| F | 2.1a | 2.2a | 2.4a |
| G | 2.2a | 2.4a | 2.5a |
| H | 2.1a | 2.2a | 2.4a |
| I | 1.8b | 2.0b | 2.7a |
| J | 2.1b | 2.2b | 2.9a |
| K | 2.1b | 2.3b | 3.0a |

From Table 5, it can be seen that with the intensification of drought, the number of new roots is gradually increasing, and the intensification of the number of new roots may be to enhance water storage capacity. Among them, under drought stress conditions, especially severe drought conditions, the number of new roots in the germplasm C, germplasm D, germplasm I, germplasm J, and germplasm K is significantly higher than that under normal water supply (Table 11). The difference in the number of new roots among other germplasms is not significant under drought stress conditions.

Determination of Length of the New Roots

The effect of drought stress on the length of new roots of *Ophiopogon japonicus* is shown in Table 6.

TABLE 6

Effect of drought stress on the length of new roots of different germplasm of *Ophiopogon japonicus* (cm)

| Serial number of germplasm resource | Normal water supply (CD) | Moderate drought (MD) | Severe drought (SD) |
|---|---|---|---|
| A | 4.1a | 4.2a | 4.6a |
| B | 4.3a | 4.5a | 2.5a |
| C | 4.0c | 5.6b | 6.5a |
| D | 4.3c | 5.7b | 6.9a |
| E | 4.2a | 4.4a | 4.7a |
| F | 4.0a | 4.1a | 4.3a |
| G | 4.2a | 4.2a | 4.6a |
| H | 4.3a | 4.8a | 4.9a |
| I | 4.2a | 4.4a | 4.8a |
| J | 4.0c | 5.0b | 6.8a |
| K | 4.1c | 5.5b | 6.9a |

As shown in Table 6, with the intensification of drought, new roots become longer and longer, possibly to enhance water storage capacity. Among them, the germplasm C, germplasm D, germplasm J, and germplasm K shows that the length of new roots of *Ophiopogon japonicus* under severe drought conditions is significantly higher than that under moderate drought conditions, and the length of new roots under moderate drought conditions is also higher than that under normal water supply (Table 11). The length of new roots in other germplasm does not show significant differences under drought stress conditions.

2.5 Determination of a Number of Leaves, Widths of the Leaves, and Growth of Leaves Length The effects of drought stress on the number of leaves, widths of the leaves, and growth of leaf length of *Ophiopogon japonicus* are shown in Tables 7 to 9.

TABLE 7

Effect of drought stress on the number of leaves of different germplasms of *Ophiopogon japonicus*

| Serial number of germplasm resource | Normal water supply (CD) | Moderate drought (MD) | Severe drought (SD) |
|---|---|---|---|
| A | 18a | 18a | 17a |
| B | 18a | 18a | 18a |
| C | 18a | 18a | 18a |
| D | 18a | 18a | 18a |
| E | 19a | 19a | 18a |
| F | 20a | 19a | 18a |
| G | 19a | 19a | 19a |
| H | 18a | 18a | 18a |
| I | 18a | 18a | 18a |
| J | 19a | 18a | 17a |
| K | 18a | 18a | 17a |

TABLE 8

Effect of drought stress on the widths of the leaves of different germplasms of *Ophiopogon japonicus* (mm)

| Serial number of germplasm resource | Normal water supply (CD) | Moderate drought (MD) | Severe drought (SD) |
|---|---|---|---|
| A | 3.1a | 3.1a | 2.9a |
| B | 3.0a | 3.1a | 3.3a |
| C | 3.1a | 3.3a | 3.0a |
| D | 3.3a | 3.2a | 3.1a |
| E | 3.3a | 3.4a | 3.3a |
| F | 3.3a | 3.4a | 3.2a |
| G | 3.0a | 3.3a | 3.0a |
| H | 3.2a | 3.1a | 3.2a |
| I | 3.0a | 3.2a | 2.9a |
| J | 3.1a | 2.9a | 3.2a |
| K | 3.2a | 3.1a | 3.4a |

TABLE 9

Effect of drought stress on the growth of leaf length of different germplasms of *Ophiopogon japonicus* (cm)

| Serial number of germplasm resource | Normal water supply (CD) | Moderate drought (MD) | Severe drought (SD) |
|---|---|---|---|
| A | 2.7a | 2.6a | 1.8b |
| B | 3.3a | 2.9a | 2.0b |
| C | 2.7a | 2.6a | 2.0b |
| D | 2.9a | 2.7a | 1.8b |
| E | 3.1a | 3.0a | 2.2b |
| F | 3.0a | 2.7a | 2.0b |
| G | 3.0a | 2.8a | 1.9b |
| H | 3.3a | 3.2a | 2.2b |
| I | 3.4a | 3.3a | 2.4b |
| J | 2.8a | 2.7a | 2.0b |
| K | 2.9a | 2.7a | 2.0b |

The effects of drought stress on the number and widths of the leaves of different germplasms of *Ophiopogon japonicus* are not significant (Tables 7 and 8), but had a significant impact on the growth of leaf length compared to *Ophiopogon japonicus* in the moderate drought and the severe drought (Table 9). It can be seen that as the degree of drought increases, *Ophiopogon japonicus* grows slowly, especially in the growth of leaves length.

3. Physiological Indicator Measurement

Five osmoregulatory substances of MDA, SOD, POD, CAT and Pro are measured. 3.1 Measurement of MDA The effect of drought stress on the MDA content of leaves of *Ophiopogon japonicus* is shown in Table 10.

TABLE 10

MDA content (nmol/mL) of different germplasms of *Ophiopogon japonicus* under drought stress

| Serial number of germplasm resource | Normal water supply (CD) | Moderate drought (MD) | Severe drought (SD) | MD-CD | SD-CD |
|---|---|---|---|---|---|
| A | 41.3 | 57.5 | 58.6 | −16.2 | −17.3 |
| B | 69.0 | 57.9 | 56.4 | 11.1 | 12.6 |
| C | 35.3 | 26.1 | 21.3 | 9.2 | 14 |
| D | 33.6 | 32.6 | 25.5 | 1.0 | 5.1 |
| E | 49.3 | 42.4 | 39.9 | 6.9 | 9.4 |
| F | 9.5 | 17.1 | 20.9 | −7.6 | −11.4 |
| G | 51.3 | 44.5 | 40.4 | 6.8 | 10.9 |
| H | 17.1 | 47.2 | 76.7 | −30.1 | −59.6 |

TABLE 10-continued

MDA content (nmol/mL) of different germplasms of *Ophiopogon japonicus* under drought stress

| Serial number of germplasm resource | Normal water supply (CD) | Moderate drought (MD) | Severe drought (SD) | MD-CD | SD-CD |
|---|---|---|---|---|---|
| I | 34.1 | 50.1 | 67.8 | −16 | −33.7 |
| J | 132.5 | 119.8 | 116.3 | 12.7 | 16.2 |
| K | 75.4 | 55.4 | 53.7 | 20 | 21.7 |

The content of MDA is a commonly used indicator in the study of plant aging physiology and resistance physiology. Membrane lipid peroxidation often occurs when plant organs are aging or damaged under stress. MDA is the final decomposition product of the membrane lipid peroxidation, and its content can reflect the degree of stress damage to plants. From Table 10, it can be seen that under drought stress, the MDA content of the germplasm A, germplasm F, and germplasm I is increased to a certain extent, which indicates that these germplasm resources have poor drought resistance when dealing with drought stress. The germplasm K, germplasm J, germplasm C, germplasm E, germplasm G, and germplasm D have relatively strong drought resistance.

3.2 Measurement of SOD

The effect of drought stress on the SOD content of leaves of *Ophiopogon japonicus* is shown in Table 11.

TABLE 11

SOD content (μmol/g) of different germplasms of *Ophiopogon japonicus* under drought stress

| Serial number of germplasm resource | Normal water supply (CD) | Moderate drought (MD) | Severe drought (SD) | MD-CD | SD-CD |
|---|---|---|---|---|---|
| A | 1696.5 | 1603.4 | 1566.1 | −93.1 | −130.4 |
| B | 1768.3 | 1648.7 | 1632.2 | −119.6 | −136.1 |
| C | 1762.2 | 1863.7 | 1887.1 | 101.5 | 124.9 |
| D | 1763.2 | 1839.1 | 1859.4 | 75.9 | 96.2 |
| E | 1576.0 | 1641.2 | 1656.6 | 65.2 | 80.6 |
| F | 1860.3 | 1870.2 | 1863.5 | 9.9 | 3.2 |
| G | 1651.0 | 1683.5 | 1724.3 | 32.5 | 73.3 |
| H | 1775.0 | 1643.7 | 1402.0 | −131.3 | −373 |
| I | 1845.2 | 1778.7 | 1639.3 | −66.5 | −205.9 |
| J | 1353.0 | 1490.6 | 1507.3 | 137.6 | 154.3 |
| K | 1649.3 | 1798.0 | 1807.5 | 148.7 | 158.2 |

SOD is an important respiratory enzyme in plants, and its activity is closely related to phenolic metabolism and plant resistance. The higher the SOD activity, the stronger the stress resistance. From Table 11, it can be seen that under drought stress conditions, the SOD content of the germplasm A, germplasm B, germplasm F, germplasm H, and germplasm I is reduced to a certain extent, which indicates that these germplasm resources have poor drought resistance when dealing with drought stress. The germplasm C, germplasm D, germplasm E, germplasm G, germplasm J, and germplasm K have relatively strong drought resistance.

3.3 Measurement of Pro

The effect of drought stress on the Pro content of leaves of *Ophiopogon japonicus* is shown in Table 12.

TABLE 12

Pro content (μg/g) of different germplasms of
*Ophiopogon japonicus* under drought stress

| Serial number of germplasm resource | Normal water supply (CD) | Moderate drought (MD) | Severe drought (SD) | MD-CD | SD-CD |
|---|---|---|---|---|---|
| A | 38.5 | 42.8 | 53.6 | 4.3 | 15.1 |
| B | 24.8 | 101.2 | 136.5 | 76.4 | 111.7 |
| C | 42.1 | 49.0 | 57.7 | 6.9 | 15.6 |
| D | 27.9 | 43.7 | 81.0 | 15.8 | 53.1 |
| E | 30.9 | 35.1 | 39.0 | 4.2 | 8.1 |
| F | 12.2 | 16.2 | 19.4 | 4.0 | 7.2 |
| G | 39.5 | 45.9 | 57.8 | 6.4 | 18.3 |
| H | 11.4 | 23.6 | 50.6 | 12.2 | 39.2 |
| I | 75.5 | 145.2 | 153.8 | 69.7 | 78.3 |
| J | 41.4 | 152.2 | 152.2 | 110.8 | 110.8 |
| K | 49.2 | 157.5 | 168.5 | 108.3 | 119.3 |

Pro is widely presented in animals, plants, microorganisms, and cultured cells. Under adverse conditions, the content of Pro in plants significantly increases. The increase of Pro to a certain extent reflects stress resistance, and germplasm with strong drought resistance often accumulates more Pro. From Table 12, it can be seen that under drought stress conditions, regardless of whether it is moderate or severe drought, the Pro content in the leaves of different germplasms of *Ophiopogon japonicus* increases compared to normal water supply treatment. Under moderate drought conditions, compared to normal water supply, the Pro content of the germplasm J increases the most, followed by the germplasm K, the germplasm B, the germplasm I, and the germplasm D. In severe drought conditions, compared to normal water supply, the Pro of the germplasm K increases the most, followed by the germplasm B, the germplasm J, the germplasm I, and the germplasm D. The results shows that the Pro content of the germplasm K, the germplasm B, the germplasm D, the germplasm I, and the germplasm J increased significantly, and their drought resistance is stronger than other germplasms.

3.4 Measurement of CAT

The effect of drought stress on the CAT content of leaves of *Ophiopogon japonicus* is shown in Table 13.

TABLE 13

CAT content (μg/g) of different germplasms of
*Ophiopogon japonicus* under drought

| Serial number of germplasm resource | Normal water supply (CD) | Moderate drought (MD) | Severe drought (SD) | MD-CD | SD-CD |
|---|---|---|---|---|---|
| A | 320.5 | 344.2 | 370.4 | 23.7 | 49.9 |
| B | 346.2 | 364.7 | 371.9 | 18.5 | 25.7 |
| C | 316.5 | 396.4 | 422.0 | 79.9 | 95.5 |
| D | 405.6 | 467.1 | 482.5 | 61.5 | 76.9 |
| E | 403.5 | 459.1 | 465.8 | 55.6 | 62.3 |
| F | 470.6 | 459.0 | 294.3 | −11.6 | −176.3 |
| G | 498.5 | 477.0 | 432.6 | −21.5 | −65.9 |
| H | 351.6 | 383.8 | 388.4 | 32.2 | 36.8 |
| I | 459.3 | 347.9 | 360.1 | −111.4 | −99.2 |
| J | 306.5 | 403.6 | 422.9 | 97.1 | 116.4 |
| K | 329.4 | 437.5b | 469.0a | 108.1 | 139.6 |

CAT is widely presented in all tissues of plants and can clear hydrogen peroxide ($H_2O_2$). It is one of the important enzymatic defense systems in plants. Therefore, the activity of CAT in plant tissues is closely related to the metabolic intensity and stress resistance of plants, and the content of CAT can reflect the drought and waterlogging resistance of plants to some extent. From Table 13, it can be seen that under drought stress conditions, regardless of whether it is moderate or severe drought, the CAT content of the germplasm A, the germplasm B, the germplasm C, the germplasm D, the germplasm E, the germplasm H, the germplasm J, and the germplasm K increases compared to normal water supply treatment, and the CAT activity of other germplasms decreases compared to normal treatment. The results shows that under drought stress, the germplasm A, the germplasm B, the germplasm C, the germplasm D, the germplasm E, the germplasm H, the germplasm J, and the germplasm K are able to resist cell membrane oxidation to a certain extent and have strong drought resistance. However, the germplasm F, the germplasm G, and the germplasm I have weaker resistance to cell membrane oxidation to a certain extent and weaker drought resistance.

3.5 Measurement of POD

The effect of drought stress on the POD content of leaves of *Ophiopogon japonicus* is shown in Table 14.

TABLE 14

POD content (μg/g) of different germplasms of
*Ophiopogon japonicus* under drought

| Serial number of germplasm resource | Normal water supply (CD) | Moderate drought (MD) | Severe drought (SD) | MD-CD | SD-CD |
|---|---|---|---|---|---|
| A | 559.5 | 486.8 | 466.1 | −72.7 | −93.4 |
| B | 407.8 | 452.8 | 465.2 | 45 | 57.4 |
| C | 555.4 | 639.6 | 655.5 | 84.2 | 100.1 |
| D | 448.5 | 502.7 | 537.0 | 54.2 | 88.5 |
| E | 571.3 | 469.8 | 436.3 | −101.5 | −135 |
| F | 493.0 | 497.6 | 399.6 | 4.6 | −93.4 |
| G | 454.1 | 422.4 | 387.5 | −31.7 | −66.6 |
| H | 529.4 | 431.6 | 424.4 | −97.8 | −105 |
| I | 415.9 | 497.4 | 520.1 | 81.5 | 104.2 |
| J | 401.1 | 559.6 | 570.2 | 158.5 | 169.1 |
| K | 550.8 | 696.2 | 702.9 | 145.4 | 152.1 |

POD is a type of oxidase widely presented in various plants. POD is one of the key enzymes in the enzymatic defense system of plants under stress conditions. It works in synergy with SOD and CAT to eliminate excess free radicals in the body, thereby improving plant stress resistance. From Table 14, it can be seen that under drought stress conditions, regardless of whether it is moderate or severe drought, the POD content of the germplasm B, the germplasm D, the germplasm I, the germplasm J, and the germplasm K all increases compared to normal water supply treatment, and the POD activity of other germplasm decreases compared to normal water supply treatment. According to the changes in POD activity of various germplasms, it is indicated that to a certain extent, the germplasm B, the germplasm D, the germplasm I, the germplasm J, and the germplasm K have stronger drought resistance than other germplasms.

4. Comprehensive Evaluation of the Fuzzy Mathematical of Drought Resistance in Different Germplasms of *Ophiopogon japonicus*

The fuzzy mathematical evaluation method is applied to comprehensively rank the growth indicators (difference in the chlorophyll content, the number of new roots, the length of the new roots, the number of leaves, the widths of the leaves, and the growth of leaf length) and the physiological indicators (MDA negative difference, SOD difference, POD difference, CAT difference, Pro difference) of the different germplasms of *Ophiopogon japonicus*, thereby screening out the drought-resistant germplasm of *Ophiopogon japonicus* with an optimal drought-resistant ability. And the fuzzy mathematical membership function calculation formula is used for quantitative transformation.

The membership function calculation formula is: $U(X_i) = (X_i - X_{min})/(X_{max} - X_{min})$, where $U(X_i)$ represents a membership function value; $X_i$ represents a measured value of a certain indicator of *Ophiopogon japonicus* germplasm; $X_{max}$ and $X_{min}$ represent a maximum value and a minimum value within the certain indictor of *Ophiopogon japonicus* germplasm, respectively.

A mathematical model is constructed for comprehensive evaluation:

two domains are constructed: $U=(U_1, U_2, U_3, \ldots U_m)$, $V=(V_1, V_2, V_3, \ldots V_n)$;

where U is a set of factors composed of comprehensive evaluation; V represents a set of membership function values for each factor.

$$R = \begin{bmatrix} 0.441 & 0.000 & 0.849 & 0.950 & 0.603 & 0.358 & 0.061 & 0.486 & 0.654 & 1.000 & 0.966 \\ 0.500 & 0.750 & 0.500 & 0.750 & 1.000 & 0.500 & 1.000 & 0.500 & 0.000 & 0.500 & 0.750 \\ 0.063 & 0.250 & 0.938 & 1.000 & 0.188 & 0.000 & 0.063 & 0.438 & 0.188 & 0.563 & 0.875 \\ 0.000 & 0.000 & 0.000 & 1.000 & 0.000 & 1.000 & 1.000 & 0.000 & 0.000 & 0.000 & 0.000 \\ 0.400 & 0.400 & 0.800 & 0.600 & 1.000 & 1.000 & 0.800 & 0.400 & 0.600 & 0.000 & 0.400 \\ 0.000 & 0.429 & 0.000 & 0.143 & 0.571 & 0.143 & 0.286 & 0.857 & 1.000 & 0.143 & 0.143 \\ 0.277 & 0.822 & 0.784 & 0.621 & 0.739 & 0.449 & 0.737 & 0.000 & 0.281 & 0.854 & 1.000 \\ 0.136 & 0.042 & 0.831 & 0.740 & 0.702 & 0.504 & 0.585 & 0.000 & 0.231 & 0.960 & 1.000 \\ 0.003 & 0.678 & 0.027 & 0.110 & 0.002 & 0.000 & 0.022 & 0.077 & 0.615 & 1.000 & 0.977 \\ 0.615 & 0.592 & 0.872 & 0.788 & 0.761 & 0.455 & 0.410 & 0.654 & 0.000 & 0.950 & 1.000 \\ 0.111 & 0.563 & 0.714 & 0.599 & 0.000 & 0.408 & 0.268 & 0.014 & 0.704 & 1.000 & 0.950 \end{bmatrix}$$

fuzzy transformation: A·R=B is taken as the mathematical model of comprehensive transformation, which is a fuzzy matrix of m×n;

a fuzzy relationship between an m-dimensional domain U and an n-dimensional domain V is: $R=(r_{ij})_{m \times n}$ (i=1, 2, ... m; j=1, 2, ... n), where A represent a fuzzy subset on U, which is the weight of the evaluation factors, and B is an evaluation result, which is a fuzzy subset on the domain V, that is, a fuzzy vector.

The growth indicators (difference in the chlorophyll content, the number of new roots, the length of the new roots, the number of leaves, the widths of the leaves, and the growth of leaf length) and the physiological indicators (the MDA negative difference, the SOD difference, the POD difference, the CAT difference, the Pro difference) are selected as evaluation factors to form the domain U, i.e., m=12. The germplasm A to the germplasm K are used, the membership function values of the average values of various indicators of 11 different germplasms of *Ophiopogon japonicus* form the domain V, i.e., n=11. The weight values of 11 evaluation factors are composed of A. A scoring method of consulting industry experts to screen and assign evaluation indicators is adopted, a specific allocation of weights is as follows:

A=[chlorophyll (0.20), the number of new root (0.05), the length of the new root (0.05), the number of leaves (0.03), the width of the leaves (0.03), and the growth of leaf length (0.04), MDA (0.12), SOD (0.12), POD (0.12), CAT (0.12), and Pro (0.12)].

The fuzzy comprehensive evaluation method is applied to evaluate different germplasms of *Ophiopogon japonicus*, thereby obtaining

A=[0.20,0.05,0.05,0.03,0.03,0.04,0.12,0.12,0.12]

In order to comprehensively analyze the drought resistance of different germplasms of *Ophiopogon japonicus*, a comprehensive evaluation is conducted on its drought resistance under different drought stress conditions.

Under Moderate Drought Stress Condition:

B=A·R={0.266,0.403,0.653,0.674,0.497,0.380,0.373, 0.2800,0.418,0.831,0.883}

According to the comprehensive evaluation results under moderate drought stress condition, the study found that the optimal comprehensive ranking of drought resistance among different germplasms of *Ophiopogon japonicus* is: the germplasm K>the germplasm J>the germplasm D>the germplasm C>the germplasm E>the germplasm I>the germplasm B>germplasm F>the germplasm G>the germplasm H>the germplasm A. That is to say, among these 11 germplasms, the germplasm K has the best drought-resistant ability, followed by the germplasm J, the germplasm D, and the germplasm C. The overall traits of drought-resistant ability of these 4 germplasms are significantly higher than that of the other 7 germplasms, which can be further observed and studied as excellent drought resistance germplasms of *Ophiopogon japonicus*.

Under Severe Drought Stress Condition:

$$R = \begin{bmatrix} 0.679 & 0.000 & 0.916 & 0.972 & 0.728 & 0.557 & 0.070 & 0.324 & 0.519 & 0.958 & 1.000 \\ 0.000 & 0.167 & 0.833 & 1.000 & 0.167 & 0.000 & 0.167 & 0.000 & 0.500 & 0.833 & 1.000 \\ 0.115 & 0.115 & 0.846 & 1.000 & 0.154 & 0.000 & 0.115 & 0.231 & 0.192 & 0.962 & 1.000 \\ 0.000 & 0.500 & 0.500 & 0.500 & 0.500 & 0.500 & 1.000 & 0.500 & 0.500 & 0.000 & 0.000 \\ 0.000 & 0.800 & 0.200 & 0.400 & 0.800 & 0.600 & 0.200 & 0.600 & 0.000 & 0.600 & 1.000 \\ 0.000 & 0.333 & 0.333 & 0.000 & 0.667 & 0.333 & 0.167 & 0.667 & 1.000 & 0.333 & 0.333 \\ 0.520 & 0.888 & 0.905 & 0.796 & 0.849 & 0.593 & 0.867 & 0.000 & 0.319 & 0.932 & 1.000 \\ 0.457 & 0.446 & 0.937 & 0.883 & 0.854 & 0.708 & 0.840 & 0.000 & 0.315 & 0.993 & 1.000 \\ 0.070 & 0.932 & 0.075 & 0.409 & 0.008 & 0.000 & 0.099 & 0.285 & 0.634 & 0.924 & 1.000 \\ 0.716 & 0.639 & 0.860 & 0.802 & 0.755 & 0.000 & 0.349 & 0.675 & 0.244 & 0.927 & 1.000 \\ 0.137 & 0.633 & 0.773 & 0.735 & 0.000 & 0.137 & 0.225 & 0.099 & 0.787 & 1.000 & 0.944 \end{bmatrix}$$

B=A·R={0.370, 0.491, 0.728, 0.756, 0.523, 0.330, 0.356, 0.263, 0.469, 0.886, 0.937}

The comprehensive evaluation results under severe drought stress condition: the optimal comprehensive ranking of drought resistance among different germplasms of *Ophiopogon japonicus* is the germplasm K>the germplasm J>the germplasm D>the germplasm C>the germplasm E>the germplasm B>the germplasm A>the germplasm G>the germplasm I>the germplasm F>the germplasm H. It can be seen that under severe drought condition, the drought-resistant ability of the germplasm K is the best, followed by the germplasm J, the germplasm D, and the germplasm C.

In summary, whether under moderate or severe drought stress conditions, the germplasm K has the best drought-resistant ability, followed by the germplasm J, the germplasm C, and the germplasm D. The drought-resistant ability of other germplasms is poor.

The above embodiments are only a description of the specific embodiments of the disclosure, and do not limit the scope of the disclosure. Without departing from the design spirit of the disclosure, all variations and improvements made by those skilled in the art to the technical solution of the disclosure should fall within the scope of protection determined by the claims of the disclosure.

What is claimed is:

1. A screening method for a drought-resistant germplasm of *Ophiopogon japonicus*, comprising steps:
   (1) collecting surviving *Ophiopogon japonicus* from a cultivated field and a wild condition under drought, introducing the collected surviving *Ophiopogon japonicus* to a conservation nursery of *Ophiopogon japonicus* germplasms, and selecting populations of the *Ophiopogon japonicus* germplasms with consistent apparent epigenetic traits in the conservation nursery of *Ophiopogon japonicus* germplasms for further evaluation after the introducing;
   (2) using an online geographic information system (GIS) software to extract rainfall including April rainfall, May rainfall, and June rainfall, of a main production area including Luxi Town, Laoma Town, Licheng Town, Lingxing Town, Liuying Town, Xinde Town, Yongming Town, and Jianshe Town in Santai County, Mianyang City, Sichuan Province, China of the *Ophiopogon japonicus* from a global climate database during a period of water demands from April to June for growth of the *Ophiopogon japonicus*, calculating monthly average rainfall from April to June, and converting the monthly average rainfall from April to June into a water supply;
   (3) setting 100±5%, 50±5%, and 35±5% of the water supply converted in the step (2) as a normal water supply, a moderate drought, and a severe drought of three water gradients according to the period of the water demands for the growth of the *Ophiopogon japonicus* under a natural condition, respectively; conducting drought stress simulation experiments on the populations of the *Ophiopogon japonicus* germplasms obtained in the step (1) under different drought conditions;
   (4) after setting the three water gradients, determining growth indicators and physiological indicators of the populations of the *Ophiopogon japonicus* germplasms under different drought stress conditions; wherein the growth indicators comprise chlorophyll, a number of new roots, lengths of the new roots, a number of leaves, widths of the leaves, and growth of leaf length, the physiological indicators comprise malondialdehyde (MDA), total superoxide dismutase (SOD), peroxidase (POD), catalase (CAT), and proline (Pro); and
   (5) applying a fuzzy mathematical evaluation method to comprehensively rank the growth indicators and the physiological indicators of the populations of the *Ophiopogon japonicus* germplasms, thereby evaluating a drought-resistant ability of the *Ophiopogon japonicus* and screening out the drought-resistant germplasm of the *Ophiopogon japonicus*,
   wherein the screening method for the drought-resistant germplasm of the *Ophiopogon japonicus* further comprises:
   planting the screened drought-resistant germplasm of the *Ophiopogon japonicus* to reduce water application amount and source under drought conditions during the period of water demands from April to June for growth of the *Ophiopogon japonicus*, so as to increase production of the *Ophiopogon japonicus*.

2. The screening method for the drought-resistant germplasm of the *Ophiopogon japonicus* as claimed in claim 1, wherein a standard of the drought in the step (1) is: a landmass of the cultivated field with high terrain and no water storage or a slope under a wild forest, and a soil moisture content of less than 20%; criteria of judging the surviving *Ophiopogon japonicus* are: plants of the *Ophiopogon japonicus* grow, and the leaves of the *Ophiopogon japonicus* appear green and not withered yellow; and the consistent apparent epigenetic trait indicates that the leaves of the plants from a same production area have a same color, and statistically significant differences in a plant height, the number of leaves, the widths of the leaves, the leaf length, and a number of tillers are non-statistical difference.

3. The screening method for the drought-resistant germplasm of the *Ophiopogon japonicus* as claimed in claim 1, wherein the monthly average rainfall from April to June is converted into a water supply daily per pot, and a converting formula is as follows:

the water supply=the monthly average rainfall from April to June (millimeter)×0.667 (square meters)÷30 (days)÷an area of an experimental container (square meters).

4. The screening method for the drought-resistant germplasm of the *Ophiopogon japonicus* as claimed in claim 1, wherein in the step (5), the growth indicators and the physiological indicators are screened and assigned based on a specific allocation of weights as follows:
   the chlorophyll (0.20), the number of new roots (0.05), the lengths of the new roots (0.05), the number of leaves (0.03), the widths of the leaves (0.03), and the growth of leaf length (0.04), MDA (0.12), SOD (0.12), POD (0.12), CAT (0.12), and Pro (0.12);
   wherein an evaluation of the fuzzy mathematical evaluation method is applied to evaluate the drought-resistant ability of the populations of the *Ophiopogon japonicus* germplasms under the moderate drought and the severe drought of the drought stress conditions, and the drought-resistant ability of the populations of the *Ophiopogon japonicus* germplasms is ranked.

* * * * *